(12) United States Patent
Vitomir

(10) Patent No.: US 11,091,401 B2
(45) Date of Patent: Aug. 17, 2021

(54) COMPOSITIONS AND METHODS FOR SELECTIVE CALCIUM SOLUBILIZATION

(71) Applicant: Protocol Environmental Solutions, Inc., Coquitlam (CA)

(72) Inventor: Sergio Vitomir, New Westminster (CA)

(73) Assignee: PROTOCOL ENVIRONMENTAL SOLUTIONS, INC., Coquitlam (CA)

( * ) Notice: Subject to any disclaimer, the term of this patent is extended or adjusted under 35 U.S.C. 154(b) by 0 days.

(21) Appl. No.: 16/715,916

(22) Filed: Dec. 16, 2019

(65) Prior Publication Data

US 2020/0199030 A1 Jun. 25, 2020

Related U.S. Application Data

(60) Provisional application No. 62/783,923, filed on Dec. 21, 2018.

(51) Int. Cl.
| | | |
|---|---|---|
| *C04B 41/46* | (2006.01) | |
| *C07C 279/02* | (2006.01) | |
| *C04B 41/00* | (2006.01) | |
| *C07C 277/00* | (2006.01) | |
| *C23F 1/14* | (2006.01) | |
| *C23F 1/46* | (2006.01) | |

(52) U.S. Cl.
CPC ............ *C04B 41/46* (2013.01); *C04B 41/009* (2013.01); *C07C 277/00* (2013.01); *C07C 279/02* (2013.01); *C23F 1/14* (2013.01); *C23F 1/46* (2013.01)

(58) Field of Classification Search
CPC ... C04B 41/46; C04B 41/009; C04B 41/5353; C04B 41/72; C23F 1/46; C23F 1/14; C07C 279/02; C07C 277/00; C07C 273/02

USPC .......................................................... 216/96
See application file for complete search history.

(56) References Cited

U.S. PATENT DOCUMENTS

| | | |
|---|---|---|
| 5,672,279 A | 9/1997 | Sargent et al. |
| 6,783,799 B1 | 8/2004 | Goodson |
| 2013/0184192 A1* | 7/2013 | Vinson ................. C11D 3/2079 510/214 |
| 2016/0137870 A1* | 5/2016 | Elgarhy .............. C04B 41/4869 510/240 |

FOREIGN PATENT DOCUMENTS

GB 1193385 A 5/1970

OTHER PUBLICATIONS

Sulfamic Acid product sheet by Hydrite Chemical Co., 2019; 2 pgs. Retrieved from SulfamicAcid_Solvents_Hydrite.com on Dec. 12, 2019.

* cited by examiner

*Primary Examiner* — Duy Vu N Deo
(74) *Attorney, Agent, or Firm* — Umberg Zipser LLP

(57) ABSTRACT

Compositions and methods are presented that selectively dissolve calcium from a variety of cementitious materials without dissolving or otherwise degrading calcium silica hydrate (CSH). Preferably, contemplated compositions comprise guanidine bisulfate hydrochloride, which can be prepared from a reaction of urea, hydrochloric acid, and sulfamic acid. Therefore, it is especially contemplated that the compositions contemplated herein are particularly suitable to clean or otherwise condition surfaces of cured concrete, Portland cement-based material, or an aggregate containing CSH.

8 Claims, No Drawings

COMPOSITIONS AND METHODS FOR SELECTIVE CALCIUM SOLUBILIZATION

This application claims priority to our U.S. Provisional Patent Application with the Ser. No. 62/783,923, which was filed Dec. 21, 2018, and which is incorporated by reference herein.

FIELD OF THE INVENTION

The present disclosure relates to compositions and methods of selective calcium solubilization, especially as it relates to calcium solubilization in cured concrete, Portland cement-based materials, and other CSH containing aggregates.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

While calcium forms a fundamental component of many cementitious materials, calcium salt/oxide scales or deposits typically need to be removed prior to application of paint or other coatings to improve contact and adhesion of the paint or coating. For example, it is well known in the art that hydrochloric acid (muriatic acid) can be used to etch concrete surfaces to thereby condition a surface in preparation for painting. However, due to the highly corrosive nature of hydrochloric acid, the user and adjoining materials or structures must be generally well protected against inadvertent exposure and run-off. Moreover, use of hydrochloric acid is also often accompanied with chlorine gas formation, which is highly undesirable.

Difficulties associated with chlorine gas generation and corrosivity of hydrochloric acid can be mitigated to at least some degree. For example, it is known that the reaction of urea with hydrochloric acid can result in the formation of urea monohydrochloride, which is a soluble salt. Urea monohydrochloride is very water soluble and displays, in solution, many of the properties of hydrochloric acid such as the ability to dissolve various oxides and calcium scale as is described, for example, in U.S. Pat. No. 5/672,279. However, urea monohydrochloride tends to indiscriminately react with various metal salts and as such will also react with/attack calcium silica hydrate (CSH, also known as C—S—H). Therefore, while urea monohydrochloride will be typically suitable for removal of lime scale from a metal surface such as from a boiler vessel, use of urea monohydrochloride with cement-based materials will in many cases result in a compromised CSH phase and attendant weakening of the cementitious structure.

Thus, even though various compositions and methods of calcium solubilization are known in the art, all or almost all of them suffer from various disadvantages. Consequently, there is a need to provide improved compositions and methods to selectively solubilize calcium from various materials of construction.

SUMMARY OF THE INVENTION

Compositions and methods that selectively solubilize calcium from various materials of constructions such as cured concrete, Portland cement-based materials and other CSH containing aggregates are disclosed. Contemplated compositions can be obtained from reacting urea with hydrochloric acid and then reacting the mixture with sulfamic acid to form a guanidine bisulphate monohydrochloride complex. Most notably, contemplated compositions and methods will preserve the CSH phase in the materials while selectively dissolving and removing other calcium forms. Additionally, contemplated compositions and methods will etch concrete surfaces without chlorine gas formation, and the resulting profile that is generated in the concrete surface is identical or comparable to one that has been etched using muriatic acid.

In one aspect of the inventive subject matter, the inventor contemplates a method of making a composition for treatment of a material that comprises calcium silica hydrate (CSH) and non-CSH calcium. Preferably, the method comprises a step of reacting urea and hydrochloric acid in a first reaction to obtain a reaction mixture, and a further step of reacting the reaction mixture with sulfamic acid to thereby generate a guanidine bisulfate hydrochloride complex.

In some embodiments, the urea and hydrochloric acid are reacted at equimolar proportions, and/or the sulfamic acid is reacted at equimolar proportions with respect to the urea. Where desired, a gelling agent, a detergent, and/or a thickener may be added. In further embodiments, the guanidine bisulfate hydrochloride complex is present in the composition in an amount of 10-65 wt %. Therefore, the composition can also be diluted prior to applying the composition to the material. Most typically, the material is concrete, masonry, stucco, or grout, and/or the non-CSH calcium is calcium chloride, calcium hydroxide, and/or calcium oxide.

Therefore, the inventor also contemplates compositions prepared by such methods. Preferably, the guanidine bisulfate hydrochloride complex is present in the composition in an amount of 10-65 wt %, and/or the composition further includes a gelling agent, a detergent, and/or a thickener.

In a further aspect of the inventive subject matter, the inventor also contemplates method of treating a material that comprises calcium silica hydrate (CSH) and non-CSH calcium, comprising a step of applying the composition of claim 9 to a surface of the material to thereby solubilize the non-CSH calcium. As noted before, contemplated materials include concrete, masonry, stucco, or grout, and the non-CSH calcium is calcium chloride, calcium hydroxide, and/or calcium oxide.

While surface application is generally performed, it should be noted that the non-CSH calcium may be solubilized to a depth of at least 3 mm below the surface. Most typically, the step of applying is performed by painting, spraying, or brushing the composition onto the surface of the material, and the composition remains at least 2 hours on the surface of the material prior to removing the solubilized non-CSH calcium. To increase contact time, the composition may further include a gelling agent, a detergent, and/or a thickener. Moreover, it is contemplated that such methods may also include a step of pre-treating the surface by mechanical abrasion or scraping, pressure washing with water, and/or degreasing.

Various objects, features, aspects, and advantages will become more apparent from the following detailed description of preferred embodiments.

DETAILED DESCRIPTION

The inventors have now discovered that various treatment compositions and methods can be provided that will achieve a desired physical surface preparation (roughening of the surface) by selectively reacting contemplated compositions with calcium salts and calcium oxides on (and even below) the surface while contemplated compositions will not react with (attack) or degrade calcium silica hydrate (CSH). As such, contemplated composition and methods are especially advantageous where concrete requires pre-treatment that is intended to remove various calcium-containing deposits/efflorescence, to etch concrete or other cementitious materials, and/or to increase adhesion of paint or other coatings or fillers.

In this context it should be noted that cured concrete can be described as a mixture of the following: CSH (the most important component of cured concrete), unreacted calcium oxide/hydroxide, calcium carbonate, unreacted silica sand, aggregate, and other optional additives such as fly ash, etc. Depending on the age of the cured concrete or exposure to various materials, the concrete may further comprise calcium salts such as calcium sulfate and/or calcium chloride. As will be described in more detail below, contemplated compositions and methods will enable methods and compositions that react with non-CSH calcium (calcium oxides, calcium hydroxides, other calcium salts that do not form part of CSH), will achieve a desired physical profile, have an increased safety profile for a user, and are safer for the environment and surrounding work area/equipment.

In one embodiment of the inventive subject matter, an exemplary composition can be prepared by the reaction of urea with hydrochloric acid, typically at an about 1:1 stoichiometric ratio. The resulting urea monohydrochloride is then further reacted with sulfamic acid, preferably at an equimolar ratio, to so yield guanidine bisulphate. The thusly obtained guanidine bisulphate will then form a guanidine bisulphate monohydrochloride complex in solution. It has been found by the inventor that such guanidine bisulphate monohydrochloride complex will selectively react with all calcium components present in concrete with the exception of CSH. While not wishing to be bound by any theory or hypothesis, the inventor contemplates that the guanidine bisulphate monohydrochloride complex is a sterically hindered complex with respect to CSH and as such will not be able to dissolve calcium present in the CSH.

Therefore, it should be appreciated that the guanidine bisulphate monohydrochloride complex in contemplated compositions and methods is able to react with all calcium components present in concrete without weakening the strength of the concrete afforded by CSH. Moreover, the physical profile that is achieved by surface treatment of a cementitious material complies with industry standards and does not contribute to the loss of CSH that would otherwise result in the weakening of the surface region of the cured concrete. Notably, an aqueous solution of contemplated complexes displays many of the hydrochloric acid properties, including the ability to dissolve various oxides and calcium scale, however, without chlorine gas formation and CSH attack. Therefore, it should be especially appreciated that contemplated compounds and compositions will be able to replace hydrochloric acid for the treatment of cementitious materials, and especially cured concrete and Portland cement.

For example, in particularly preferred aspects of the inventive subject matter, the surface of cured concrete, Portland cement-based materials, and other CSH containing aggregates can be treated with contemplated compositions to remove calcium salts and/or oxides, typically to a depth of between about 0.5-1.5 mm, or between about 1.0-2.0 mm, or between about 1.5-3 mm, or between about 2.5-5 mm. Most typically, surface treatment will be in the range of between 10-30 minutes, or between 30-120 minutes, or between 120-300 minutes, or between 5-12 hours, or between 12-24 hours, or even longer. Treatment will typically be performed by direct application to the surface, for example, by spraying, rolling, painting, brushing, etc., which may be enhanced by one or more agents that form a viscous fluid, a gel or otherwise adherent layer. Advantageously, contemplated compositions achieve the same chemical surface preparation as industry standard physical profiles, however, without the creation of chlorine or fumes as a by-product of the reaction that occurs. Thus, surfaces treated with the compositions presented herein can the subsequently washed and dried, and then coated with paint or other coating materials and/or filler. Viewed from a different perspective, contemplated compositions are suitable to selectively remove calcium salts, various calcium oxides and hydroxides and scale as well as calcium salts with (in)organic anion portions. As noted before, treatment of cured concrete, Portland cement-based materials, and other CSH containing aggregates with contemplated compositions will leave CSH intact. Thus, the total amount of surface exposed CSH will be after treatment no less than 90%, or no less than 95%, or no less than 97%, or no less than 98%, or no less than 99%, as compared to before treatment. On the other hand, the total amount of surface exposed non-CSH calcium will be after treatment no more than 30%, or no more than 20%, or no more than 10%, or no more than 5%, or no more than 2%, as compared to before treatment.

Most typically, but not necessarily, contemplated compositions will be prepared by reacting equimolar quantities of urea with hydrochloric acid to form urea monohydrochloride. However, it should be appreciated that molar ratios other than 1:1 are also deemed suitable, and contemplated ratios include 15:1 to 1:15, or 10:1 to 1:10, or 7:1 to 1:7, or 5:1 to 1:5, or 3:1 to 1:3 or 2:1 to 1:2. For example, where non-equimolar ratios are used, a moderate molar excess (1.5-fold, or 2-fold, or 3-fold, or 5-fold) of hydrochloric acid may be employed where additional impurities are present on the materials that are to be treated or where some CSH degradation is acceptable. Most typically, the reaction between urea and hydrochloric acid is mildly exothermic and will be substantially complete after about 10-120 minutes. As will be readily appreciated, the concentration of urea and hydrochloric acid can vary considerably, and preferred concentrations will be between 0.01M and 5M (and even higher), or between 0.1M and 5M, or between 0.5M and 5M, or between 1M and 5M, or between 2M and 5M. Most typically, the reaction is performed in an aqueous solvent system, and most preferably in an aqueous solution of hydrochloric acid and urea (which may be added as solid or aqueous solution).

Upon completion of the reaction between urea and hydrochloric acid, sulfamic acid is added to the reaction product to form in situ a guanidine monohydrochloride complex, and more specifically, a urea monohydrochloride complex with guanidine bisulphate. Therefore, the ratio of sulfamic acid to urea is once more typically equimolar. Alternatively, however, the ratio of sulfamic acid to urea may also between 15:1 to 1:15, or 10:1 to 1:10, or 7:1 to 1:7, or 5:1 to 1:5, or 3:1 to 1:3 or 2:1 to 1:2. In most cases, the reaction times between the sulfamic acid and urea monohydrochloride is between 1 and 10 minutes, or between 10 minutes and 1 hour, or between 1 and 6 hours, or between 6-12 hours, preferably at ambient temperature (e.g., 20° C.) to allow for the formation of the guanidine monohydrochloride complex. Notably, use of sulfamic acid to remove calcium carbonate from boiler metal surfaces has been known. However, such use often required high temperatures and relatively long contact times. Moreover, sulfamic acid has also been reported to be incompatible with various other compounds, including amines. In the present compositions, however, sulfamic acid can be combined with urea monohydrochloride to form guanidine monohydrochloride complex, which is chemically stable and afforded high selectivity with regard to calcium salt solubilization while not dissolving CSH. Thus, it should be appreciated that contemplated compositions provide the strength of hydrochloric acid without the undesirable side effects (such as chlorine gas evolution and CSH degradation) and significantly increase calcium solubilizing capability and speed of sulfamic acid when used alone.

Alternative bases in addition to or replacing at least part of the urea include numerous weak bases, and especially nitrogenous bases. Among other suitable bases, contemplated bases acetylurea, hydroxyurea, semicarbazide; mono-, di-, or tri(alkyl or aryl)urea, various alkanolamines such as triethanolamine, diethanolamine, or monoethanolamine, various alkylamines such as methylamine, ethylamine, propylamine, or butylamine, various dialkylamines and alkyldiamines (e.g., ethylenediarnine), alkyltriamines, alkyltetramines, and trialkylamines. Still further contemplated compounds include polymers with amino or (alkyl or aryl)amino substituent groups, including (mono or di)alkylaminoalkylacrylates, and (mono- or di)alkylaminoalkylmethacrylate, as well as various polymers with nitrogen containing heterocyclic groups (e.g., pyridine, pyrimidine, imidazole, tetrazole, pyrazine, quinoline, isoquinoline, indole, isoindole, benzimidazole, purine, pyrrole, is pyrazole, quinazoline, pyridazine, pyrazine, cinnoline, phthalazine, quinoxaline, xanthine, hypoxanthine, and pteridine). Moreover, alternate compounds also include various amides, including formamide, acetamide, acrylamide, as well as polymers and copolymers of acrylamide, and cyclic amides such as caprolactam. Further contemplated polymers may also include pyrrolidone such as polyvinyl pyrollidone, copolymers of vinyl pyrollidone, methacrylamide, polymethacrylamide, and copolymers of methacrylamide.

Of course, it should also be noted that while a subsequent reaction with sulfamic acid is generally preferred, guanidine (or guanidine hydrochloride) may be used as a starting material that is then reacted with a sulfate or bisulfate salt. Where needed, additional hydrochloric acid may be added in appropriate molar quantities (e.g., equimolar or other ratios as noted above). Therefore, it should be recognized that the inventors contemplate various methods of making the compounds and composition of the inventive subject matter. Among other options, it is generally preferred to react urea with hydrochloric acid and then to further react the reaction mixture with sulfamic acid to so obtain the guanidine bisulfate monohydrochloride complex. In alternative options, guanidine or guanidine hydrochloride may be reacted with a sulfate or bisulfide salt (or even sulfuric acid) to yield the same guanidine bisulfate monohydrochloride complex.

Moreover, it is generally contemplated that the compositions presented herein will be in liquid form, which may further include thickening agents, detergents, and other functional ingredients. While the PHOSITA is well aware of various suitable thickeners, especially preferred thickening agents include various water-soluble agents, and especially polymeric agents. Thus, suitable thickening agents include hydroxy methyl, -ethyl, or -propyl cellulose at a desired amount, typically between 1-10% by weight, such as 0.1-3.0% by weight, or 3.0-6.0% by weight, or 6.0-9.0% by weight. Likewise, the PHOSITA will be readily apprised of appropriate detergents/surfactants and especially preferred surfactants include anionic detergents, cationic detergents, amphoteric detergents, alone or in combination. Most typically, such detergents/surfactants will be present in an amount of between 0.01 wt % to about 5 wt %, such as 0.01-0.1 wt %, or between 0.1-1.0 wt %, or between 1.0-5.0 wt %.

In at least some embodiments, contemplated compositions may also be in form of a kit in which sulfamic acid is provided as one ingredient and urea hydrochloride as another, separate ingredient. In such case, the two ingredients may be mixed at the site of use, or may be separately applied (e.g., sulfamic acid application before urea monohydrochloride application). Of course, it should also be recognized that contemplated compositions may be at least partially dehydrated into a solid or concentrate that can then be reconstituted to a working concentration.

Consequently, the inventors contemplate a method of treating a material (e.g., cured concrete, Portland cement-based material, or aggregate containing CSH) comprising soluble calcium and CSH in which a surface of the material is contacted with a composition that comprises guanidine bisulfate hydrochloride. Viewed from a different perspective, the inventors also contemplate a method of dissolving soluble calcium in a material comprising CSH without attacking CSH in the materials in which a surface of the material is contacted with a composition that comprises the guanidine bisulfate hydrochloride.

For example, especially contemplated compositions for treatment of a material comprising CSH and soluble calcium will include guanidine bisulfate hydrochloride, optionally in combination with a gelling agent, a detergent, and/or a thickener. Thus, contemplated compositions may be formulated as a liquid or a solid. Most typically, such compositions are prepared by reacting urea (or other suitable nitrogenous base) with hydrochloric acid to obtain a reaction mixture that is further reacted with sulfamic acid to so form guanidine bisulfate hydrochloride. Typically, but not necessarily, the urea and hydrochloric acid are reacted at equimolar proportions, and/or the sulfamic acid is reacted at equimolar proportions with respect to the urea. Where desired, a gelling agent, a detergent, and/or a thickener may be added. Alternatively, guanidine hydrochloride may be reacted with a bisulfate salt to produce a guanidine bisulfate hydrochloride containing composition.

Contemplated compositions are particularly desirable where they are applied to a CSH containing cementitious material or surface that also includes various (poorly water soluble) calcium species, and especially various calcium salts such as calcium chloride. For example, concrete or other masonry may exhibit primary or secondary efflorescence, and contemplated compositions may be used to remove these from the cementitious material or surface.

Likewise, concrete or other cementitious material may have been to sulfuric acid/sulfate attack, carbonation, or other chemical (typically acidic) degradation, Consequently, leached calcium species (e.g., as calcium sulfate) may be present on and even within the concrete or other cementitious material that will not contribute to the mechanical strength and/or barrier function. Thus, contemplated compositions may be used to remove such calcium species prior to restoration (or other treatment) of the cementitious material.

In most cases, contemplated compositions will be applied to the (surface of the) concrete or other cementitious material in an amount that will solubilize at least 50%, or at least 60, or at least 70%, or at least 80%, or at least 90%, or at least 95% of the calcium species as a soluble calcium that can then be simply rinsed off the concrete or other cementitious material. While the reaction of contemplated compositions with the calcium species will commence upon contact, it is generally preferred to extend the duration of the contact between the calcium species and contemplated compositions over a period of at least 1 minute, or at least 10 minutes, or at least 20 minutes, or at least 30 minutes, or at least 1 hour, or at least 3 hours, or even longer (particularly where a gelling agent is included). For example, suitable contact times may be between 1 and 10 minutes, or between 10 minutes and 1 hour, or between 1 and 6 hours, or between 6 and 12 hours, and even longer.

After a desired period of contact, the concrete or other cementitious material may then be rinsed with water or any other wash fluid (e.g., aqueous detergent solution) that will assist in removing the solubilized calcium and contemplated composition. Most typically, the concrete or other cementitious material will then be dried and subsequently treated with a filler or barrier material, and/or paint.

EXAMPLES

The following examples are provided as exemplary guidance and are not intended to limit the scope of the inventive subject matter presented herein.

Urea is reacted with hydrochloric acid, typically preserving the stoichiometry as described above. The resulting urea monohydrochloride is then further reacted with sulfamic acid. The reaction first will yield guanidine bisulphate which in the next step will attach by means of complexation reaction to unreacted urea monohydrochloride. The resulting complex is a solution of guanidine bisulphate monohydrochloride. More specifically, the quantity of reagents are chosen such that the final concentration of the guanidine bisulphate (which is typically in complex with unreacted monohydrochloride) is between 10-65 wt %, more typically between 30-60 wt %, and in some preferred embodiments between 45-50 wt %. For example, final compositions may include between about 10-25 wt % guanidine bisulphate monohydrochloride complex, or between about 20-30 wt % guanidine bisulphate monohydrochloride complex, or between about 30-40 wt % guanidine bisulphate monohydrochloride complex, or between about 40-60 wt % guanidine bisulphate monohydrochloride complex. As will be readily appreciated, additional inactive components such as one or more detergents, thickeners, pH stabilizers, etc. may be added in conventional manner and quantities.

For example, in one typical embodiment of the inventive subject matter, urea is added in an equimolar amount in a mixing tank that was charged with diluted hydrochloric acid (20 BE, about 31.8 wt % HCl). The mixture was agitated until the urea was completely dissolved. In a next step sulphamic acid was added (in equimolar amount relative to the urea) to the tank and mixed for 45 minutes to allow for the reaction to complete. One or more surfactants added after this stage as well as thickeners under continuous mixing.

Thusly prepared compositions can then be applied by brushing or spraying to a cementitious surface (e.g., concrete with primary or secondary efflorescence, concrete after exposure to sulfates or sulfuric acid, aged in-service concrete, masonry, Portland cement, mortar, stucco, grout, etc.). Most typically, the surface will be pre-treated by mechanical abrasion or scraping, pressure washing with water, and degreasing as needed. Depending on the quantity of non-CSH calcium and the desired depth of treatment, the composition will be left in contact with the cementitious surface for between 2-12 hours, after which the surface is washed (using a sponge, spray, or pressurized stream) with water. Once washed, the cementitious surface is then dried prior to further application of paint, filler, or other surface treatment.

The recitation of ranges of values herein is merely intended to serve as a shorthand method of referring individually to each separate value falling within the range. Unless otherwise indicated herein, each individual value is incorporated into the specification as if it were individually recited herein. Where a numeral is qualified by the term "about", deviations of +/−10% of that numeral are encompassed (e.g., 'about 20 wt %' refers to a range of 18-22 wt %, inclusive). All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:
1. A method of selectively solubilizing non-CSH calcium in a material that comprises calcium silica hydrate (CSH) and non-CSH calcium, comprising:
applying a composition to a surface of the material to thereby selectively solubilize the non-CSH calcium without degrading the CSH,
wherein the composition is prepared by (i) reacting urea and hydrochloric acid in a first reaction to obtain a reaction mixture, and (ii) reacting the reaction mixture with sulfamic acid to thereby generate a guanidine bisulfate hydrochloride complex; and wherein the composition comprises the guanidine bisulfate hydrochloride complex in an amount of 10-65 wt %, and wherein the composition comprises the urea hydrochloride and the sulfamic acid at a ratio of between 3:1 and 1:3.

2. The method of claim 1 wherein the material is concrete, masonry, stucco, or grout.

3. The method of claim 1 wherein the non-CSH calcium is solubilized to a depth of at least 3 mm below the surface.

4. The method of claim 1 wherein the non-CSH calcium is calcium chloride, calcium hydroxide, and/or calcium oxide.

5. The method of claim 1 wherein the step of applying is performed by painting, spraying, or brushing the composition onto the surface of the material.

6. The method of claim 1 wherein the composition remains at least 2 hours on the surface of the material prior to removing the solubilized non-CSH calcium.

7. The method of claim 1 wherein the composition further comprises a gelling agent, a detergent, and/or a thickener.

8. The method of claim 1 further comprising a step of pre-treating the surface by mechanical abrasion or scraping, pressure washing with water, and/or degreasing.

* * * * *